Figure 1A:
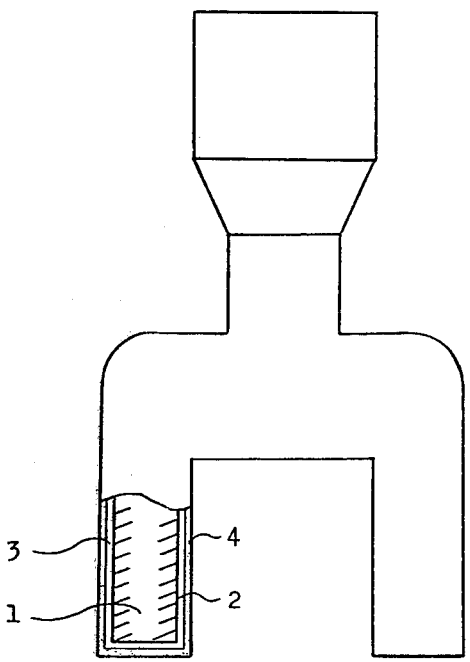

United States Patent [19]

Aoyagi et al.

[11] 4,146,936
[45] Apr. 3, 1979

[54] IMPLANTS FOR BONES, JOINTS AND TOOTH ROOTS

[75] Inventors: Masaya Aoyagi; Mikio Hayashi, both of Kawanishi; Yasuyuki Yoshida, Toyonaka; Yoshiaki Yao, Takatsuki, all of Japan

[73] Assignee: Sumitomo Chemical Company Limited, Osaka, Japan

[21] Appl. No.: 755,137

[22] Filed: Dec. 29, 1976

[30] Foreign Application Priority Data

Dec. 30, 1975 [JP] Japan .................................. 50-158745

[51] Int. Cl.² ......................... A61F 1/24; A61C 13/00; A61C 13/30
[52] U.S. Cl. ...................................... 3/1.91; 3/1.913; 128/92 C; 128/92 CA; 32/10 A; 427/2; 427/423
[58] Field of Search ..................... 3/1.9–1.913; 128/92 C, 92 CA, 92 G; 32/10 A

[56] References Cited

U.S. PATENT DOCUMENTS

| | | | |
|---|---|---|---|
| 3,787,900 | 1/1974 | McGee | 128/92 C X |
| 3,789,029 | 1/1974 | Hodosh | 3/1.9 X |
| 3,790,507 | 2/1974 | Hodosh | 3/1.9 X |
| 3,892,648 | 7/1975 | Phillips et al. | 3/1.9 X |
| 3,918,100 | 11/1975 | Shaw et al. | 3/1.9 |
| 3,922,155 | 11/1975 | Broemer et al. | 3/1.9 X |
| 4,051,598 | 10/1977 | Sneer | 128/92 C X |

FOREIGN PATENT DOCUMENTS

2306552  8/1974  Fed. Rep. of Germany .............. 3/1.91

OTHER PUBLICATIONS

"Development of Ceramic & Ceramic Composite Devices for Maxillofacial Applications" by T. D. Driskell et al, Journal of Biomedical Materials Research Symposium, No. 2 (Part 2), 1972, pp. 353 & 354.

*Primary Examiner*—Ronald L. Frinks
*Attorney, Agent, or Firm*—Birch, Stewart, Kolasch and Birch

[57] ABSTRACT

An improved implant for a bone, a joint and tooth root comprising a metallic base material and a coating layer of hydroxyapatite which is formed by thermally sprayed hydroxyapatite powder or a mixture of hydroxyapatite powder and ceramic powder around the outer surface of the metallic base material, optionally a layer of a bonding agent and further a layer of ceramics are formed between the metallic base material and the layer of hydroxyapatite. The implant has a sufficient mechanical strength (e.g. impact strength) and further a good affinity to tissues of living bodies and is useful for implantation in various bones including tooth roots in living bodies.

21 Claims, 4 Drawing Figures

U.S. Patent    Apr. 3, 1979    4,146,936

IMPLANTS FOR BONES, JOINTS AND TOOTH ROOTS

BACKGROUND AND SUMMARY OF THE INVENTION

The present invention relates to the improvement of endosseous implants for living bodies. More particularly, it relates to an improved implant for a bone, a joint and tooth root comprising a metallic base material and a layer of a hydroxyapatite formed on the base material.

The so-called implantology which comprises insertion of artificial materials such as artificial organs, artificial blood vessels, artificial joints, artificial bones and artificial tooth roots into living bodies so as to recover lost parts of living bodies or their functions has been in the limelight in recent years. It is said that a trial of implantation goes back to ancient times. Particularly in these ten-odd years, a huge number of treatments by implantation have been performed on bones and tooth roots to afford good results in the remedy of the defects or recovery of functions thereof. However, an artificial bone or tooth root which can satisfy the necessary requirements as the material for living bodies, i.e. affinity to living bodies, safety, excellent mechanical strength (e.g. pressure resistance or impact strength) and durability, has not yet been obtained.

As metallic materials conventionally used for preparation of artificial bones or tooth roots, mainly cobalt-chromium alloys, stainless steel, titanium and tantalum are exemplified. On the other hand, as ceramic materials, titanium oxide, aluminum oxide, calcium oxide-aluminum oxide, aluminum oxide-silicon dioxide glass, silicon dioxide-sodium oxide-calcium oxide-phosphorus pentaoxide glass (bioglass) or carbon materials are exemplified, and bioceramics such as apatite [$Ca_5(Cl, F)(PO_4)_3$] have been recently taken note of.

Although metallic materials are excellent in mechanical strength, particularly in impact strength, they are faulty in the affinity to tissues of living bodies. For example, when a metallic implant is used, metal ions are dissolved out therefrom in living bodies and affect a toxic action to bone cells around the implant. Furthermore, the bone-formation is obstructed probably because of too large a thermal conductivity of the metallic implant. Among the metallic materials, tantalum is particularly superior in a corrosion-resistance and hence has been employed as fixing plates for skulls or fractured parts of bones and implants for jawbones, but this metal is difficult to be processed. To the contrary, ceramic materials show generally a good affinity to bones, and bone tissues penetrate into fine pores of the ceramic materials to afford a strong fixation, without reaction between the ceramic material and the tissue. Besides, they are also excellent in durability, that is, they are resistant to corrosion decomposition. But on the other hand, they possess a poor impact strength. Moreover, these artificial materials are entirely heterogeneous to the components of the hard tissues such as bones or tooth roots, and hence, they are merely a dead material in the living bodies, while they do not show a toxic effect thereto. Then, there is taken note of the apatites which are similar to the components of bones or tooth roots. Particularly, hydroxyapatite, which is a main component of the inorganic materials in the hard tissues such as bones or tooth roots, is absorbed into the living body and is simultaneously replaced by the newly grown bone in the host (i.e. the human body to be implantated), and therefore, the hydroxyapatite has a particularly excellent affinity to the tissues of living bodies. However, the hydroxyapatite has also a defect, i.e. a poor impact strength, much like other ceramic materials.

As a result of the present inventors' studies, it has now been found that desirable implants having a sufficient impact strength and hence an excellent breakresistance while retaining the advantages of ceramic materials and hydroxyapatite as above-mentioned can be obtained by combining a metallic base material and a layer of hydroxyapatite.

An object of the present invention is to provide an improved implant having excellent mechanical strength and an affinity to living bodies.

Another object of the present invention is to provide a method for improving metallic implants by coating a hydroxyapatite or a mixture thereof with ceramics on the surface of a metallic base material to form a layer of the hydroxyapatite.

A further object of the present invention is to provide an improved implant for various bones including tooth roots which exhibits good durability.

These and other objects of the present invention will be apparent from the following description.

The implant of the present invention comprises a metallic base material having an excellent mechanical strength and a coating layer of hydroxyapatite which is formed by thermally spraying hydroxyapatite powder (I), a mixture of hydroxyapatite powder and ceramic powders (II) or ceramic powders and subsequent hydroxyapatite powder (III) around the outersuface of the metallic base material.

The present invention will be hereinafter explained in detail with reference to the accompanying drawings, which are merely illustrative of an embodiment of the invention but the present invention is not limited thereto.

Figure 1B:
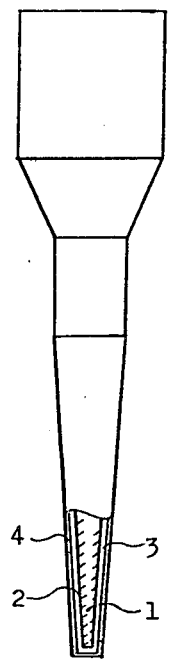
Figure 2A:
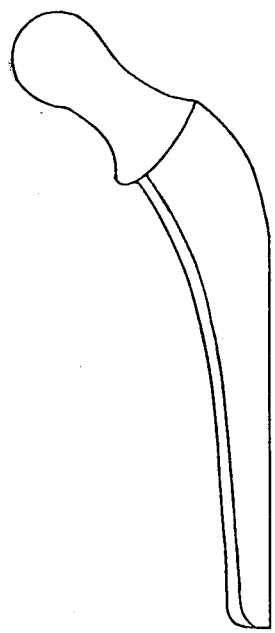
Figure 2B:
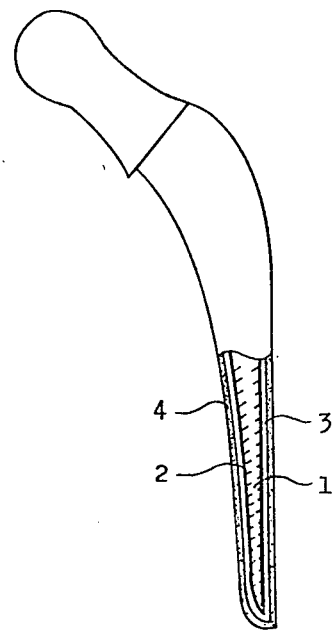

FIG. 1 is a schematic view of an embodiment of the implant for jawbone, wherein (A) is a front view thereof and (B) is a side view thereof, and FIG. 2 is a schematic view of an embodiment of the implant useful as an artificial head of an artificial coxa, wherein (A) is an oblique view thereof and (B) is a side view thereof.

In the figures, 1 is the metallic base material having an excellent mechanical strength, 2 is a thermally sprayed layer of a bonding agent, 3 is a thermally sprayed layer of ceramic powders, and 4 is a thermally sprayed layer of hydroxyapatite powder or a mixture of ceramic powders and hydroxyapatite powder. The thermally sprayed layer 2 is optionally provided in order to improve the adhesion between the metallic base material 1 and the thermally sprayed layers 3 and 4, and the thermally sprayed layer 3 is optionally provided only when the thermally sprayed layer 4 is composed of the hydroxyapatite powder alone, but is not provided when the layer 4 is composed of the mixture of ceramic powders and hydroxyapatite powder.

The implant of the present invention is characterized in that the base material is composed of a metallic material having an excellent mechanical strength and there is provided a coating layer composed of a hydroxyapatite having an excellent affinity to the tissues of living bodies alone or a mixture thereof with ceramic powders around the outersurface of the base material.

As the metallic implant material in the invention, there may be employed any conventional one used as an artificial material for bones and dental roots which exhibits little or no harmful influences on living bodies and possesses an appropriate mechanical strength. Specific examples are a cobaltchromium-nickel alloy, a cobalt-chromium-molybdenum alloy, stainless steel 18-8, 316 L, titanium, tantalum, etc.

The bonding agent may be a self-bonding type material which can microscopically bond, even onto a smooth non-porous substrate at moderate substrate temperatures. Suitable examples of the bonding agent are powders of molybdenum, tantalum, niobium, nickel-chromium-aluminum powdery mixture, nickel-aluminum powdery mixture, or the like.

The ceramics used in the present invention include any conventional thermal spray materials which are usually used for the treatment of the surface of metals by a thermal spray method in order to give them a corrosion resistance, wear resistance or the like, for instance, metal oxides, such as aluminum oxide ($Al_2O_3$), titanium oxide ($TiO_2$), zirconium oxide ($ZrO_2$), silicon dioxide ($SiO_2$), stannic oxide ($SnO_2$), phosphorus pentaoxide ($P_2O_5$), calcium oxide ($CaO$), or diboron trioxide ($B_2O_3$), which are used along or in a mixture of two or more thereof.

The hydroxyapatite used in the present invention includes synthetic hydroxyapatite and hydroxyapatite obtained from organisms (bio-hydroxyapatite). For instance, the synthetic hydroxyapatite may be prepared by reacting $Ca_3(PO_4)_2$ with an excess amount of CaO in steam at a high temperature of 900° to 1300° C. (dry synthesis) or by reacting calcium (0.5 mol/l) and an aqueous solution of phosphoric acid at a pH value of 7.1 to 7.4 and at 37° C. (wet synthesis). The bio-hydroxyapatite may be prepared by using as the starting material bones or teeth of various animals (e.g. cattle, horse, dog, chicken, rabbit, etc.), i.e. by heating the hard tissue of the bones or teeth at around 800° C. in air, dipping the resultant in a boiling liquid of ethylene diamine, whereby the organic materials contained therein are dissolved and removed, and then burning the organic materials with oxygen, which is converted into a plasma at a low temperature, by using a low temperature ashing device.

The implant of the present invention can be applied to various parts in living bodies as a bone, a joint or a tooth root, for instance, within teeth, bones or mucouse membrances or under periostea. The shape of the matallic base material is not limited to a specific one, but may be in various forms, such as pin, screw, blade, anchor, plate, mesh, or the like.

In the method of the production of the present implants, the metallic materials may be formed by any conventional methods, but is usually formed by casting method. The metallic meterial is molten, subjected to a casting, and then trimmed and ground appropriately to give a formed base material. The formed base material thus obtained is subjected to grit blasting and thereon is formed coating layers of (a) (i) a bonding agent and (ii) hydroxyapatite powders, (b) (i) a bonding agent and (ii) a mixture of ceramic powders and hydroxyapatite powders, or (c) (i) a bonding agent, (ii) ceramic powders and (iii) hydroxyapatite powders, in order, by a thermal spray method (i.e. by blowing and laminating thereon the layer-forming material molten or nearly molten by a technique of combustion or with electric energy), preferably by a plasma spray method (i.e. by applying the layer-forming material in the form of a plasma jet of a supersonic electromagnetic fluid having a high temperature obtained by arcing). The bonding agent, however, is not necessarily used. The portion not to be coated is previously masked by coating with a masking material such as a marking ink or an aluminum-made adhesive tape prior to subjecting it to grit blasting. The product thus coated with the layer(s) of hydroxyapatite and ceramics may be used as the implant as it is, or may be used after the surface thereof is ground, or further after baked at a temperature of 900 to 1300° C. in air or in a vacuum.

The size and shape of the metallic base material are determined so that the implant is fit to the portion to be applied. The bonding agent is usually applied in a thickness of not more than 200$\mu$, preferably 50 to 150$\mu$. The layer of the hydroxyapatite or the mixturre of hydroxyapatite and ceramics provided on the layer of bonding agent is usually applied in a thickness of not more than 300$\mu$, preferably 100 to 250$\mu$ in case of the above (a) or (b), i.e. in case of the layer composed of the hydroxyapatite alone or the layer composed of a mixture of hydroxyapatite and ceramics. When both of the layer composed of ceramics and the layer composed of hydroxyapatite are provided on the layer of the bonding agent as in case of (c), each layer is applied in a thickness of not more than 300$\mu$, preferably 100 to 150$\mu$.

When a mixture of ceramic powders and hydroxyapatite powder is applied, the mixing ratio is not specifically limited, but they are usually mixed in a ratio of 10% by weight of the hydroxyapatite powder and the remainder of the ceramic powders, preferably 30 to 70% by weight of the hydroxyapatite powder and the remainder of the ceramic powders.

The implants of the present invention have the following advantages. That is, the thermally sprayed layers of the ceramics and the hydroxyapatite have some pores, but the pores do not pass through the layers, i.e. do not reach to the metallic base material, and hence, the tissue of living body do not contact with the metallic base material and no toxic action of the metallic material exhibits. The thermally sprayed layers of the ceramics and the hydroxyapatite have an excellent affinity to the tissue of living bodies and the newly formed bone cells are penetrated into the pores in the thermally sprayed layers, and thereby, the implant is strictly fixed to the living body. The layer of the hydroxyapatite is provided at the outermost layer of the implant and directly contacts to the tissue of living body, and hence, it is absorbed into the tissue and is simultaneously replaced by the newly grown bone. The newly grown bone penetrates into the pores of the thermally sprayed layer of ceramics, wherein the implant is further strictly fixed to the living body.

In addition to the excellent affinity of the hydroxyapatite to the tissues of living bodies, the implant of the present invention has the advantage that it does not require any bone cement as used in conventional artificial tooth roots, artificial bones and artificial joints, since the surface of the thermally sprayed layer of the implant is uneven and the bone tissue grows around the uneven surface, which exhibits an anchoring effect.

The following examples are given to illustrate the present invention more precisely, but they should not be interpreted to restrict the present invention thereto.

EXAMPLE 1

A metallic base material for implant is produced from a cobalt-chromium-nickel alloy (Nobilium, trade name of Nobilium Co.). That is, the cobalt-chromium-nickel alloy is molten by high frequency heating and subjecting to centrifugal casting. The casted product is ground to give a metallic base material (weight: 0.7 g).

The metallic base material thus obtained is subjected to grit blasting (blasting agent: Metcolite VF, trade name of Metco Inc., England, pressure: 30 psi) with a ventiblast apparatus (mammoth type, made by Metco Inc.). Using a plasma spray apparatus (provided with a 6MR-630 type electric power supplier, made by Metco Inc.), argon-hydrogen-plasma jet flame (arc electric current: 500 Amp) is generated, and firstly nickel-aluminum composite powder (Metco Powder No. 450, made by Metco Inc.; a self-bonding type bonding agent) is thermally sprayed onto the metallic base material so as to form a layer having a thickness of about 80μ onto the whole surface of the metallic base material, and secondly hydroxyapatite powder (white powder produced by the dry synthesis method, specific gravity: 3.2, particle size: not more than 100μ) is thermally sprayed so as to form the second layer having a thickness of about 200μ in average. The resulting product is baked by heating at 1100° C. for 10 minutes to give the desired implant.

The implant was embedded into a tibia of a pig, and observation by a X-ray fluoroscopy was effected for 3 months. As the result, there was observed the growth of dense bone around the implant.

EXAMPLE 2

In the same manner as described in Example 1, an implant is produced by thermally sprayed onto the metallic base material the nickel-aluminum composite powder as used in Example 1 so as to form the first layer (thickness: 80μ) and then a mixture of 70% by weight of hydroxyapatite and 30% by weight of aluminum oxide (Metco Powder No. 105, made by Metco Inc.) so as to form the second layer (thickness: 200μ).

EXAMPLE 3

In the same manner as described in Example 1, an implant is produced by thermally sprayed onto the metallic base material the nickel-aluminum composite powder as used in Example 1 so as to form the first layer having a thickness of about 80μ onto the whole surface of the metallic base material, secondly aluminum oxide power so as to form the second layer having a thickness of about 150μ in average, and thirdly hydroxyapatite powder so as to form the third layer having a thickness of about 150μ in average, and then baking the resultant.

The implant thus obtained was embedded into a tibia of a pig, and observation by a X-ray fluoroscopy was effected for 3 months. As the result, there was observed a skeletal structure of the newly grown bone contacted directly to the implant, which proves the growth of bone around the implant.

EXAMPLE 4

In the same manner as described in Example 1, an implant is produced by thermally sprayed onto the metallic base material the nickel-aluminum power so as to form the first layer (thickness: 80μ), secondly aluminum oxide powder so as to form the second layer (thickness: 150μ), and thirdly cattle bone powder so as to form the third layer (thickness: 150μ), and the baking the resultant.

The cattle bone powder used above is prepared by heating cattle bone at 800° C. in air, by which the organic materials contained therein are burnt and removed off, and pulverizing the resultant to give powders having a particle size of not more than 100μ.

The implant thus obtained was embedded into a tibia of a pig, and observation by X-ray fluoroscopy was effected for 3 months. As the result, there was observed the growth of dense bone around the implant.

EXAMPLE 5

In the same manner as described in Example 3 except that a titanium alloy is used as the metallic base material, there is prepared an implant useful for jawbone as shown in FIG. 1.

The implant was embedded into the lower jawbone of a dog, and observation by a X-ray fluoroscopy was effected for 3 months. As the result, there was observed a skeletal structure of the newly grown bone around the implant. Besides, according to the macroscopic observation, there was observed no abnormal symptom in the paradental tissues.

EXAMPLE 6

In the same manner as described in Example 3 except that a cobalt-chromium alloy is used as the metallic base material, there is prepared in implant useful for artificial head of artificial coxa as shown in FIG. 2.

The implant was embedded into the coxa of a dog, and observation by a X-ray fluoroscopy was effected for 3 months. As the result, there was observed no abnormal symptom.

What is claimed is:

1. An implant for members of living bodies comprising a metallic base material, a layer of a material selected from the group consisting of hydroxyapatite and a mixture of hydroxyapatite and ceramics and a layer of a bonding agent formed between the metallic base material and the layer of hydroxyapatite or a mixture of hydroxyapatite and ceramics, said bonding agent being selected from the group consisting of molybdenum, tantalum, niobium, nickel-chromium-aluminum powdery mixture and nickel-aluminum powdery mixture.

2. The implant according to claim 1, wherein the layer of a mixture of hydroxyapatite and ceramics comprises not less than 10% by weight of hydroxyapatite and the remainder of ceramics.

3. The implant according to claim 2, wherein the layer of a mixture of hydroxyapatite and ceramics comprises 30 to 70% by weight of hydroxyapatite and the remainder of ceramics.

4. The implant according to claim 1, wherein a layer of ceramics is formed between the metallic base material and the layer of hydroxyapatite.

5. the implant according to claim 4, wherein the layer of ceramics and the layer of hydroxyapatite are each formed in a thickness of not more than 300μ.

6. The implant according to claim 5, wherein the thicknesses of the layers of ceramics and hydroxyapatite are each in the range of 100 to 150μ.

7. The implant according to claim 1, wherein the layer of a bonding agent is formed in a thickness of not more than 200μ, and the layer of hydroxyapatite or a mixture of hydroxyapatite and ceramics is formed in a thickness of not more than 300μ.

8. The implant according to claim 7, wherein the thickness of the layer of a bonding agent is in the range of 50 to 150μ, and the thickness of the layer of hydroxyapatite or a mixture of hydroxyapatite and ceramics is in the range of 100 to 250μ.

9. The implant according to claim 4, wherein a layer of a bonding agent is further formed between the metallic base material and the layer of ceramics.

10. The implant according to claim 9, wherein the layer of a bonding agent is formed in a thickness of not more than 200μ and the layers of ceramics and hydroxyapatite are each formed in a thickness of not more than 300μ.

11. The implant according to claim 10, wherein the thickness of the layer of a bonding agent is in the range of 50 to 150μ, and the thicknesses of the layers of ceramics and hydroxyapatite are each in the range of 100 to 150μ.

12. The implant according to claim 1, wherein the metallic base material is made of a member selected from the group consisting of a cobalt-chromium-nickel alloy, a cobalt-chromium-molybdenum alloy, stainless steel 18-8, 316 L, titanium and tantalum.

13. The implant according to claim 1, wherein the ceramics are a member selected from the group consisting of aluminum oxide, titanium oxide, zirconium oxide, silicon dioxide, stannic oxide, phosphorus pentaoxide, calcium oxide, diboron trioxide, and a mixture thereof.

14. The implant of claim 1, wherein the implant is for a bone.

15. The implant of claim 1, wherein the implant is for a joint.

16. The implant of claim 1, wherein the implant is for a tooth root.

17. The implant of claim 1, wherein the metal base is in the form of a pin.

18. The implant of claim 1, wherein the metal base is in the form of a blade.

19. The implant of claim 1, wherein the metal base is in the form of an anchor.

20. The implant of claim 1, wherein the metal base is in the form of a plate.

21. The implant of claim 1, wherein the metal base is in the form of a mesh.

* * * * *